US00PP32220P3

(12) United States Plant Patent
Rasch

(10) Patent No.: US PP32,220 P3
(45) Date of Patent: Sep. 22, 2020

(54) APPLE TREE NAMED 'FR1063'

(50) Latin Name: *Malus domestica*
Varietal Denomination: FR1063

(71) Applicant: Frederic A Rasch, Conklin, MI (US)

(72) Inventor: Frederic A Rasch, Conklin, MI (US)

( * ) Notice: Subject to any disclaimer, the term of this patent is extended or adjusted under 35 U.S.C. 154(b) by 0 days.

(21) Appl. No.: 15/932,940

(22) Filed: May 25, 2018

(65) Prior Publication Data

US 2020/0008335 P1 Jan. 2, 2020

(51) Int. Cl.
*A01H 6/08* (2018.01)
*A01H 6/74* (2018.01)

(52) U.S. Cl.
USPC ..... Plt./161
CPC ..... *A01H 6/7418* (2018.05)

(58) Field of Classification Search
USPC ..... Plt./161
CPC ..... A01H 6/7418
See application file for complete search history.

*Primary Examiner* — Anne Marie Grunberg

(57) ABSTRACT

A new and distinct variety of apple tree, 'FR1063', originating as a whole tree mutation of an unknown variety *Malus domestica*. This new variety is unique from other apple cultivars because of its coloring, flavor and ripening date.

6 Drawing Sheets

Latin name of the genus and species of the plant claimed: *Malus domestica*.

DESCRIPTION OF RELATED APPLICATIONS

The new variety, 'FR1063' differs from other varieties in the following characteristics:

A. The fruit of the new variety is almost full red with a subtle stripe, ripening in early October, resembling no other known variety.

BACKGROUND OF THE INVENTION

A new and distinct variety of apple tree originating as a whole tree mutation of an *Malus domestica*, hereinafter referred to as 'FR1063'.

SUMMARY OF THE INVENTION

This new and distinct variety of apple tree was discovered in Conklin, Mich. as a whole tree mutation in an orchard planted in 1998. The new variety was noticed because the fruit was less red and started coloring about one week behind than the other trees in the orchard.

Observations during the next two seasons confirmed that the fruit and tree were completely different than the varieties surrounding it, including 'Gala', 'Honeycrisp', and 'Jonagold'. The mature fruit of the new variety finishes to a 40 to 50% red blush. The new variety matures in early October in central Michigan one to three weeks behind 'Gala', 'Honeycrisp', and 'Jonagold'.

In April of 2007, buds were taken from the original limb and reproduced by grafting on M9 (an unpatented selection) rootstock in Conklin. Mich. The new variety has remained true to the description herein contained. The new variety has not been grown on its own root.

DESCRIPTION OF THE DRAWINGS

The accompanying photographs show typical specimens of the new variety as depicted in color as nearly true as is reasonably possible in color illustrations of this character. These specimens were obtained at Chester Township, Conklin, Mich.

DETAILED BOTANICAL DESCRIPTION

Figure 1:
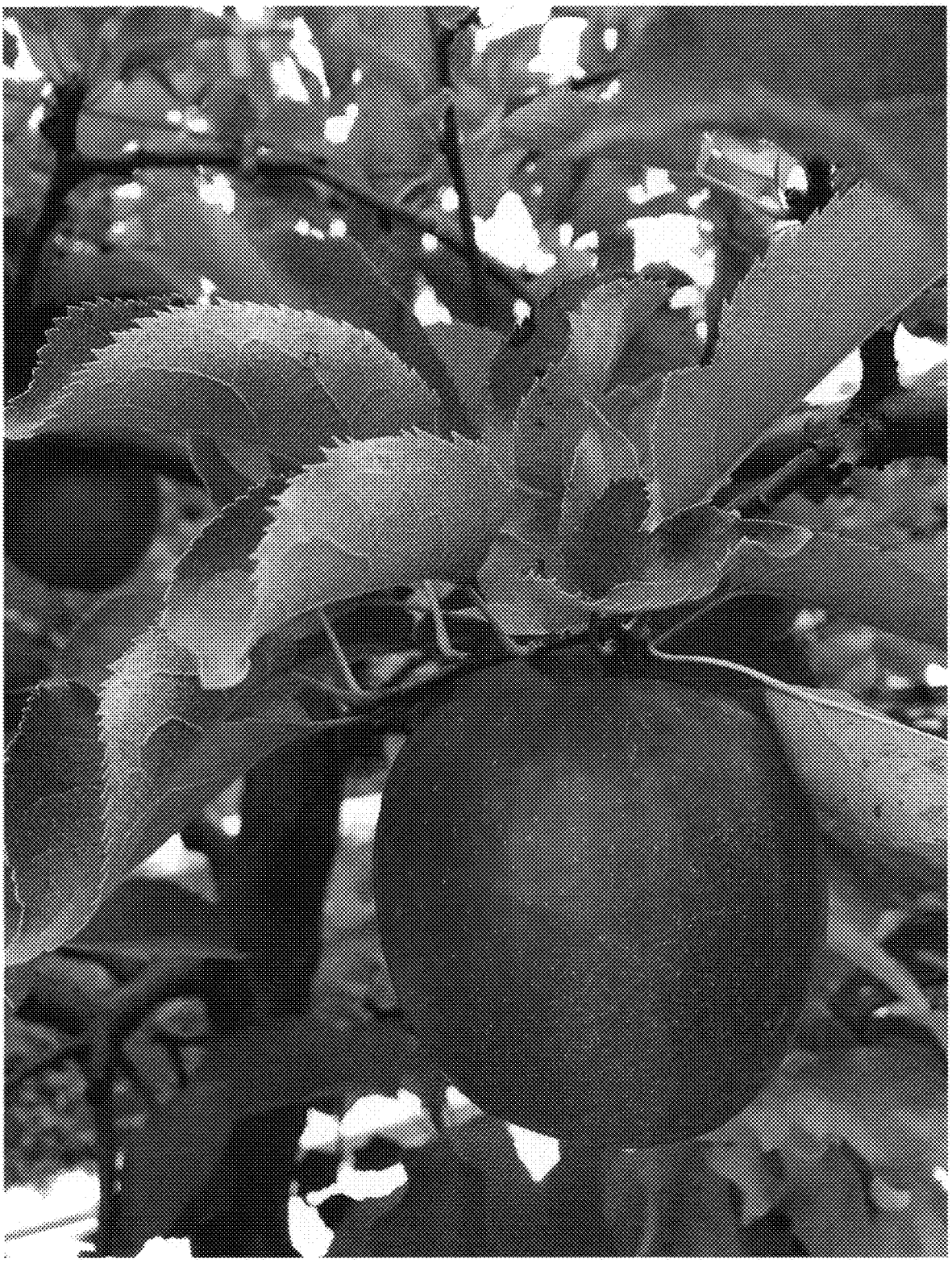
FIG. 1 illustrates the fruits and foliage of the new variety at maturity.
Figure 2:
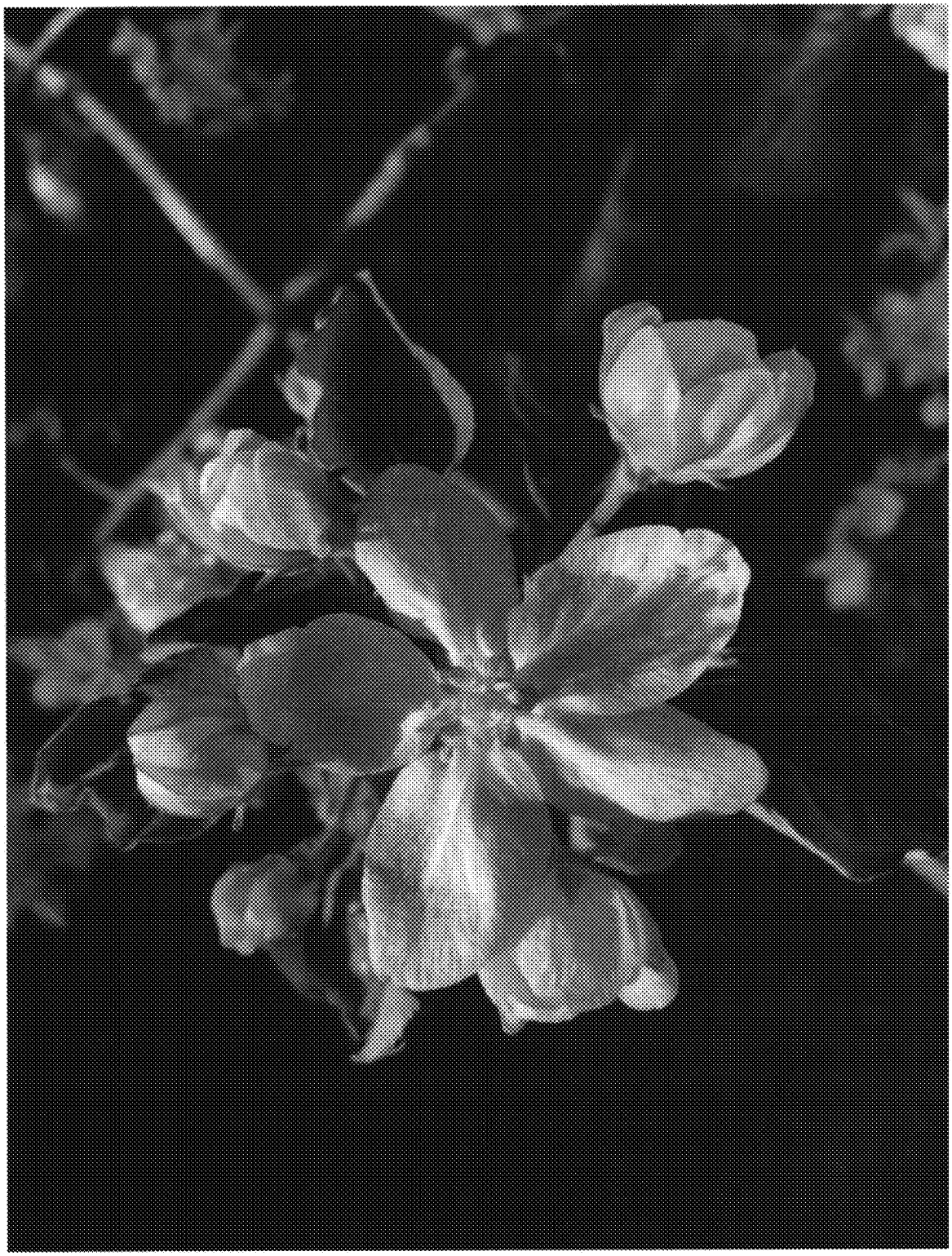
FIG. 2 illustrates blossoms and buds of the new variety.
Figure 3:
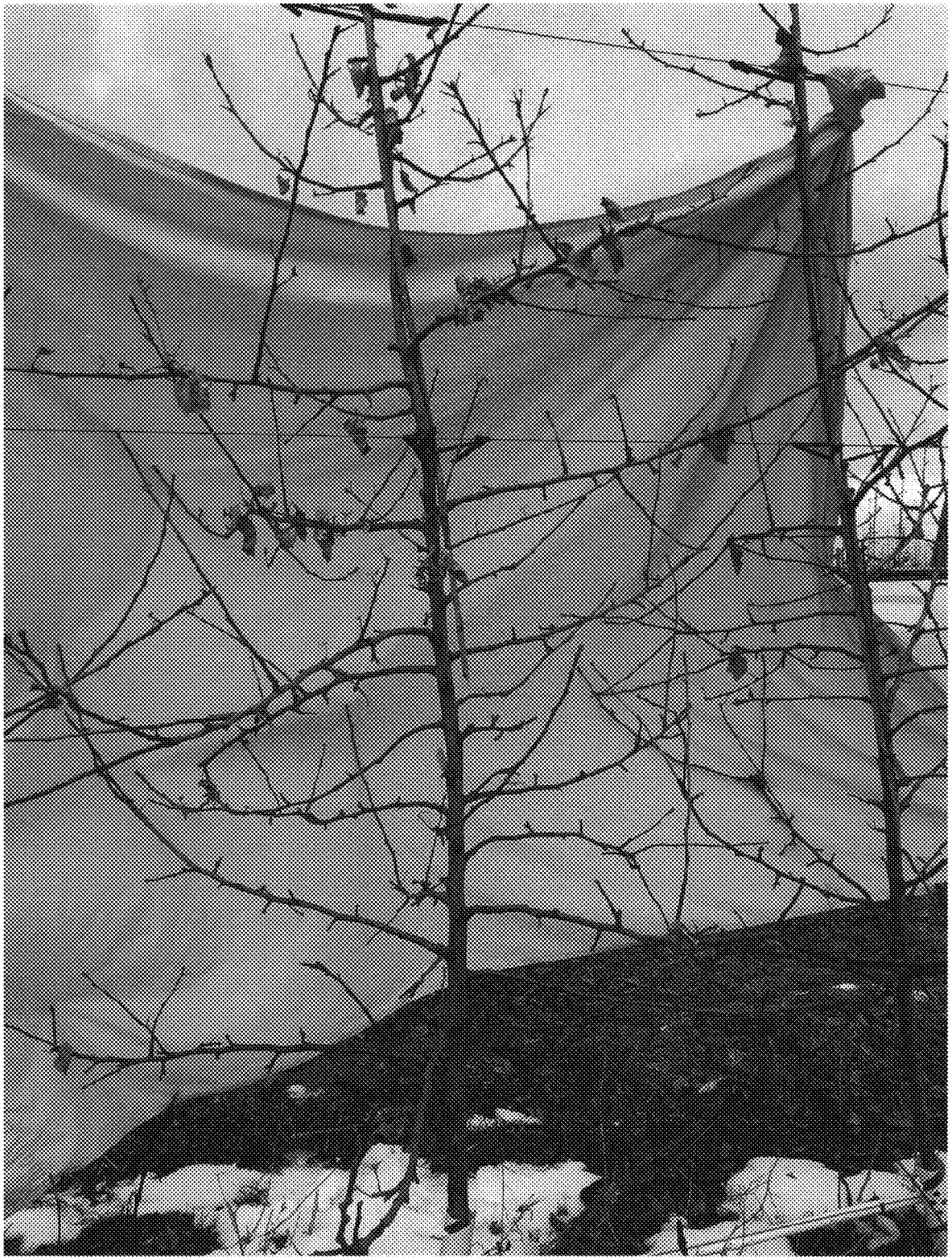
FIG. 3 illustrates a dormant tree of the new variety.
Figure 4:
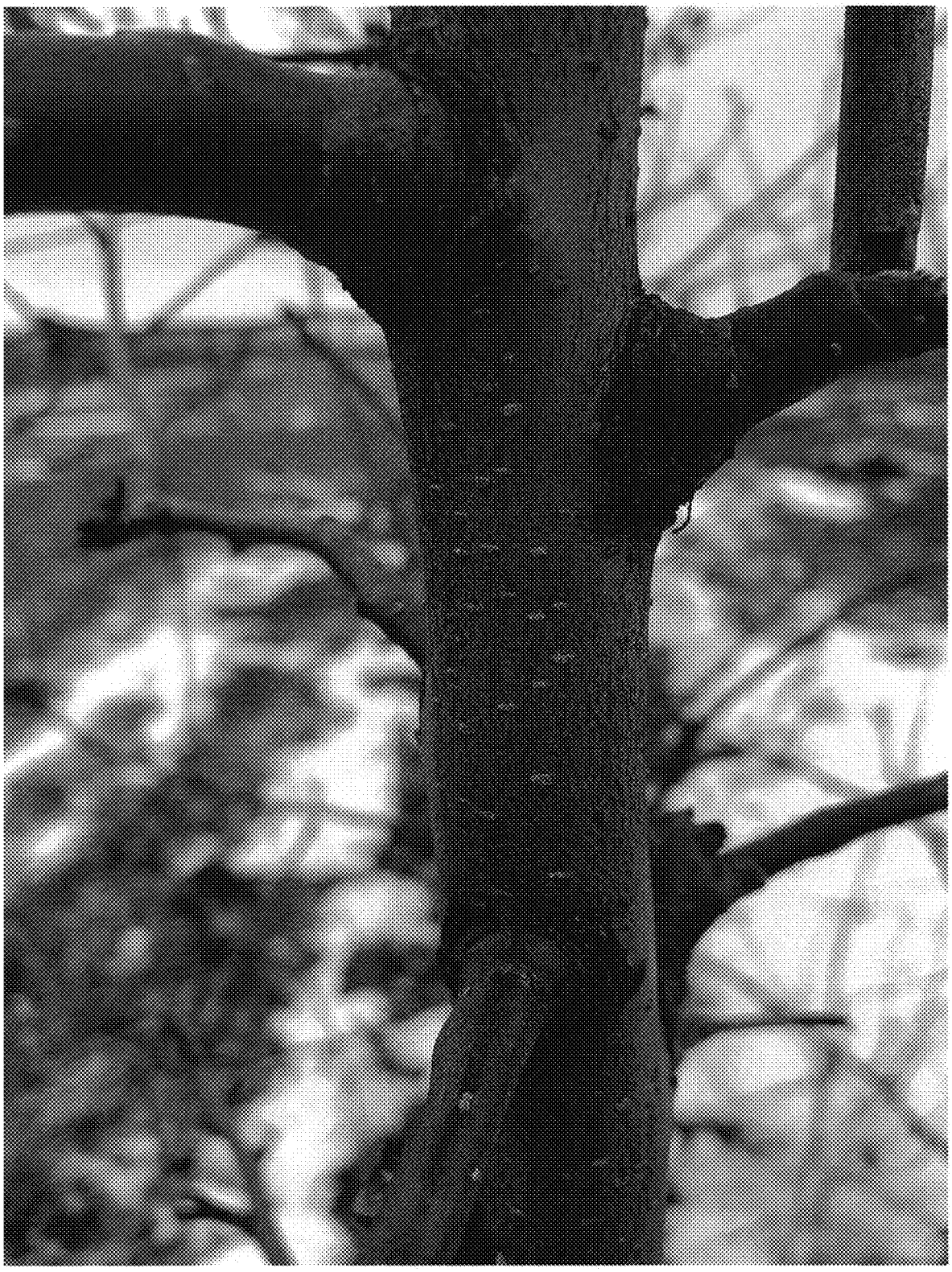
FIG. 4 illustrates the trunk and lenticels of the new variety.
Figure 5:
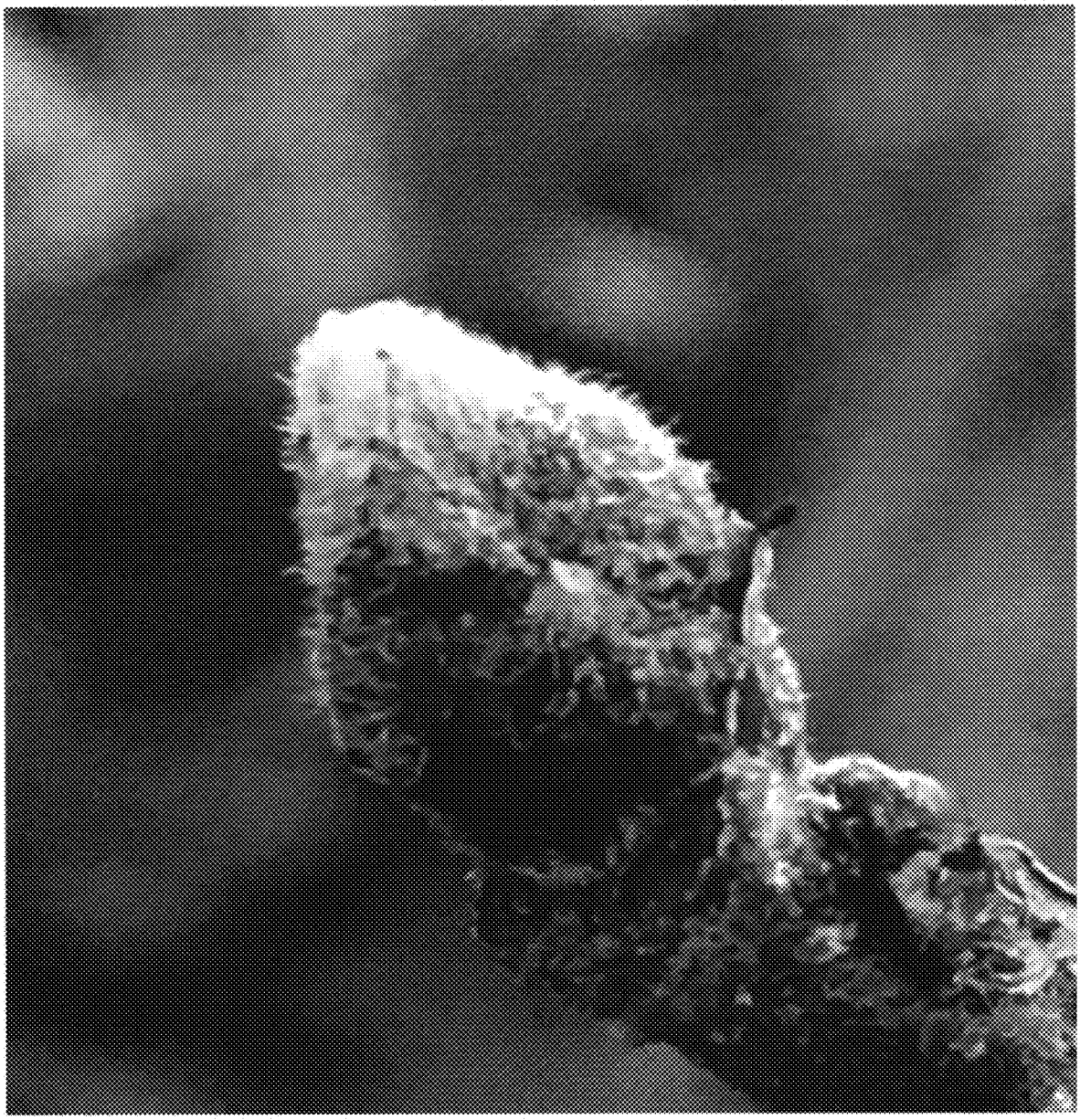
FIG. 5 illustrates a terminal bud of the new variety.
Figure 6:
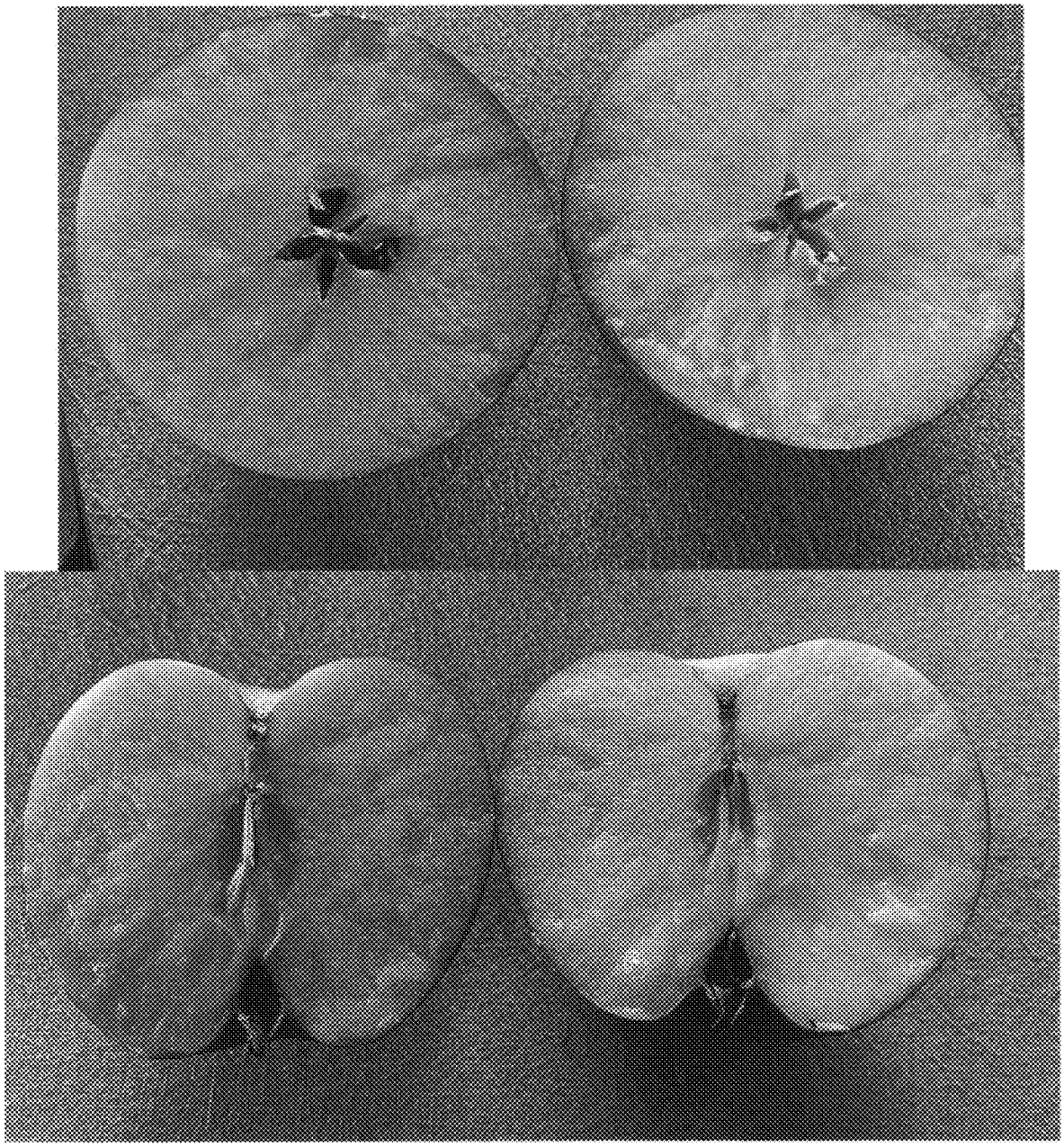
FIG. 6 illustrates a transverse and diagonal sections of the new variety.

A detailed description of the 'FR1063' cultivar follows using The Royal Horticultural Society of London Colour Chart, 1986 edition, for color identification except where general color terms are sufficient.

Parentage: A whole tree mutation of unknown parentage. Locality of the original discovery and observations is Chester Township, Conklin, Mich.

Tree:

*Age.*—5 years.
*Size.*—Large, height 2 m, width 1 m.
*Vigor.*—Vigorous, yearly growth averages 0.5 m.
*Density.*—Open.
*Form.*—Flat to slightly upright.
*Production.*—Very productive, averaging 800 bushels per acre.
*Growth type.*—Non-spur.
*Bearing.*—Annual.

Trunk:

*Size.*—85 mm in diameter at 90 cm above ground level.
*Surface.*—Smooth.
*Bark color.*—Gray 201D.
*Lenticels.*—Length 1 cm, width 1 mm.
*Lenticel color.*—Gray 201D.

*Lenticel density.*—1 per $cm^2$. Averaging 2 to 3 lenticels in an area of 4 cm×4 cm.

Branches:

3 *year old branch.*—20 mm in diameter, color Grayed Brown 199C.

2 *year old branch.*—10 mm in diameter, color Grayed Brown 199A.

1 *year old branch.*—6 mm in diameter, color Grayed Brown 199A.

Lenticels: 0.1 mm in diameter, round, color Grayed Brown 199A.

Leaves:

*Size.*—Length 95 mm, width 55 mm.

*Texture.*—Crisp, thin.

*Form.*—Broadly ovate.

*Base.*—Cuneate.

*Apex.*—Acute.

*Upper surface pubescence.*—Absent.

*Lower pubescence.*—Very fine.

*Upper surface color.*—Green 139A.

*Lower surface color.*—Green 138A.

*Leaf blade attitude in cross section.*—Very cupped in a majority of leaves.

*Leaf blade margin.*—Straight with an occasional ripple.

*Venation.*—Pinnate, 11 to 13 veins, mainly alternate, color Grayed Green 195B.

*Mid-vein.*—Upper surface color Green 145A, lower surface color Green 145A.

*Margin.*—Dentate.

*Petiole length.*—32 mm.

*Petiole width.*—2 mm.

*Petiole upper color.*—Grayed Green 195B.

*Petiole lower color.*—Green 144B.

*Petiole groove.*—Very shallow, depth 0.1 mm at base of petiole.

*Stipules.*—Very fine, at the base of the petiole on most leaves.

*Stipule color.*—Green 139A.

*Leaf glands.*—None observed.

Leaf buds:

*Length.*—2 mm.

*Width.*—2 mm.

*Color.*—Grayed Green 197B.

*Leaf but shape.*—Triangular, length 8 mm, width 7 mm.

*Placement on branch.*—Opposite, spiral, applied.

*Internode distance.*—20 mm to 25 mm on one-year old wood.

*Pubescence.*—Very faint.

*Growth pattern of one-year old shoots.*—Held at a 90 degree angle to the trunk.

Spurs: Present on 2 year and older wood.

*Length.*—10 mm to 15 mm.

*Width.*—4 mm.

*Color.*—Greyed Green 197A.

Flowers:

*Bloom period.*—Second week of May in central Michigan.

*Presentation.*—Showy.

*Fragrance.*—Faint.

*Fertility.*—Somewhat self-fertile, a good pollen source for other apple varieties blooming in the same period.

*Pollination requirements.*—Requires pollen from other variety blooming in the same period.

*Pollen.*—Present, abundant.

Flowers at popcorn stage:

*Pedicle.*—Length 19 mm to 22 mm, diameter 0.2 mm.

*Pedicel color.*—Grayed Green 195B.

*Bud.*—Length 9 mm, width 8 mm.

*Bud color.*—Red 43A.

Flowers at full bloom:

*Corolla diameter.*—Large, 75 mm to 85 mm when fully open.

*Numbers of flowers per cluster.*—3 to 5.

*Inflorescence type.*—Umbellate.

Petals:

*Arrangement.*—Overlapping, number 5.

*Color.*—White 155D with a blush on 20% to 40% of the petal surface of Red 55B.

*Petal veins.*—Indistinct coloration of White 155A.

*Shape.*—Rounded.

*Margin.*—Somewhat waved with an occasional point at the apex, cupped with a basin 5 mm deep from the edge to the center of the petal.

*Size.*—Length 30 mm, width 20 mm.

*Texture.*—Crisp.

*Pedicel.*—Length 27 mm to 28 mm, width 2 mm, color Yellow Green 145D.

*Sepals.*—5 in number, wedge shaped, sharply pointed, length 5 mm, width 2 mm, color Yellow Green 145D.

*Filaments.*—Length 10 mm, width 0.3 mm, color White 155D at junction with anther.

*Anthers.*—Length 2 mm, width 0.1 mm, color Yellow 4C.

*Pistil.*—Held slightly lower than anthers in a majority of blossoms.

*Ovary.*—Length 4 mm, width 1.5 mm, pubescent, color Green White 157A.

*Stigma.*—Width 1 mm, pubescent, color Green White 157A.

*Style.*—Length 3 mm, width 1 mm, color White 157C.

Fruit:

*Maturity when described.*—Firm ripe.

*Date of picking.*—October $4^{th}$ to $7^{th}$ in Conklin, Kent County, Mich., generally harvested in two pickings.

*Size.*—Axial diameter 80 mm, transverse diameter 95 mm.

*Fruit weight (firm ripe).*—250 g.

*Form.*—Uniform, symmetrical, regular, blocky, round.

*Eye.*—Obtuse, deep, depth 19 mm, width 35 mm.

*Basin.*—Symmetrical, abrupt at base, wide, depth, 21 mm, width 30 mm.

*Calyx.*—Open, segments persistent, erect, outer and inner surfaces Russet at calyx end: present in some fruit, extending to top of basin, pubescent, color Grayed Green 193A.

*Type of bearing.*—On spurs and long shoots.

Skin:

*Young fruit.*—Color at 20 mm size: Red 53 B.

*Thickness.*—Medium thick.

*Texture.*—Very smooth, glossy with medium cuticle wax.

*Tendency to crack.*—Slight.

*Lenticels.*—White, inconspicuous, small, few in number.

*Color.*—40 to 50% blush of Red 46A with subtle striping of Red 46B, with the remainder of fruit a blush of Yellow 11B.

*Ground color.*—Yellow 11B.

Flesh:

*Aroma.*—Sweet, aromatic.

*Color.*—Yellow 11D.

*Texture.*—Firm, tender, fine, crisp.

*Eating quality.*—Best, very juicy.

*Brix at eating maturity.*—16.5%.

*Flesh pressure at eating maturity.*—18+pounds.

Core:

*Bundle area.*—Medium to ovate, cordate, symmetrical at base.

*Bundle.*—Inconspicuous, green, alternate above stamens.

*Carpillary area.*—Distinct, medium size.

*Calyx tube.*—Slightly urn shaped, open.

*Depth of tube to shoulder.*—17 mm.

*Styles.*—Distinct, pubescent.

*Stamens.*—One distinct whorl, small.

*Axillary cavity.*—Wanting.

*Seed cells.*—Walls thin, tough, length 10 mm, width 5 mm.

*Longitudinal section.*—Broadly ovate.

Seeds:

*Number perfect.*—8 to 12.

*Number in one cell.*—2 to 4.

*Length.*—10 mm.

*Breadth.*—4 mm.

*Form.*—Obtuse.

*Color.*—Brown 200B.

Stem:

*Length.*—35 mm.

*Width.*—3 mm.

*Color.*—Grayed Green 194A with mottling Grayed Red 181C.

*Use.*—Processing, fresh market, dessert.

*Shipping quality.*—Good.

*Keeping quality.*—Excellent, 90 to 120 days in common storage, 6 to 10 months in controlled atmosphere storage.

Tree winter hardiness: Average for an apple variety. Tree is hardy to −10° to −25° F.

Bud winter hardiness: −15° to −20° F., dependent on the stage of development of the bud.

Drought tolerance: Average for an apple variety. Normal requirements average ½" of rain per week. Severe drought adversely affects fruit size and quality.

Disease resistance: Susceptible to fire blight (*Erwinia amylovora*) and other bacterial diseases. Moderately susceptible to apple scab (*Venturia inaequalis*), powdery mildew (*Podosphaera leucotricha*), and other fungal diseases.

I claim:

1. A new and distinct variety of apple tree, *Malus domestica*, substantially as herein shown and described.

* * * * *